US005498740A

United States Patent [19]
Dermeik et al.

[11] Patent Number: 5,498,740
[45] Date of Patent: Mar. 12, 1996

[54] COMPOSITIONS COMPRISING REACTION PRODUCTS OF PHOSPHITES, QUINONES AND ISOCYANATES

[75] Inventors: Salman Dermeik, Augsburg; Martina Wanner, Neusäss; Karl-Heinz Lemmer, Augsburg; Reinhold Braun, Schwabmünchen, all of Germany

[73] Assignee: Ciba-Geigy Corporation, Tarrytown, N.Y.

[21] Appl. No.: 26,963

[22] Filed: Mar. 5, 1993

[30]     Foreign Application Priority Data

Mar. 14, 1992 [DE] Germany .......................... 42 08 235.8

[51] Int. Cl.⁶ ............................ C07F 9/02; C07C 261/00
[52] U.S. Cl. ................. 558/89; 560/26; 560/27; 560/29; 560/32
[58] Field of Search ................. 558/89; 560/26, 560/29, 32, 27

[56]              References Cited

U.S. PATENT DOCUMENTS

| | | | |
|---|---|---|---|
| 2,577,281 | 12/1951 | Simon et al. | 260/2.5 |
| 2,691,566 | 10/1954 | Kvalnes et al. | 8/115.5 |
| 2,691,567 | 10/1954 | Kvalnes et al. | 8/115.5 |
| 2,691,567 | 10/1954 | Kvalnes et al. | 8/115.5 |
| 2,733,229 | 1/1956 | Brace | 260/73 |
| 2,926,145 | 2/1960 | McConnell et al. | 260/2 |
| 4,380,593 | 4/1983 | Van Bonin et al. | 521/163 |

FOREIGN PATENT DOCUMENTS

| | | |
|---|---|---|
| 269058 | 3/1969 | Austria . |
| 937956 | 1/1956 | Germany . |
| 2312090 | 9/1974 | Germany . |
| 3109352 | 9/1982 | Germany . |
| 458137 | 1/1975 | U.S.S.R. . |
| 1147713 | 3/1985 | U.S.S.R. . |

OTHER PUBLICATIONS

Müller, "Methoden Der Organischen Chemie", Band XII/2 pp. 368–370.
Sanin, et al. "The Reaction of Dialkyl Phosphites wtih Quinones" Chem Abs Trans, vol. 54, 20940a, pp. 479–483 (1960).
J. Org. Chem. vol. 38, No. 12, 1973 pp. 2151–2152.
J. Org. Chem. vol. 22 (1957) pp. 1282–1283.
J. Org. Chem. vol. 81 (1959) pp. 4338–4343.
Chem Abst. vol. 54, 20940a pp. 479–483 (1950).

*Primary Examiner*—Kimberly J. Kestler
*Attorney, Agent, or Firm*—Kevin T. Mansfield

[57]              ABSTRACT

Compositions which, in the form of aqueous dispersions or of solutions in organic solvents, are suitable for the treatment of fiber materials can be obtained by reaction of organic phosphites and quinones and subsequent reaction with mono-, di- or polyisocyanates. Flame-retardant properties having a good permanence are imparted, above all, to fabrics comprising polyester fibers by this procedure.

9 Claims, No Drawings

COMPOSITIONS COMPRISING REACTION PRODUCTS OF PHOSPHITES, QUINONES AND ISOCYANATES

The invention relates to compositions which can be obtained by reaction of phosphites with quinones and subsequent reaction of the resulting products with isocyanates. It furthermore relates to the use of such compositions for the treatment of fiber materials.

It is known that phosphorus-containing products can be employed in the flameproofing sector. Thus, for example, DE-A 31 09 352 describes polymeric intumescent compositions. U.S. Pat. No. 2,577,281 describes flameproofing agents based on phosphonic acid.

It is furthermore known that fiber materials can be treated with compositions comprising phosphorus compounds in order to impart to them flame-retardant properties. Fiber materials in the form of woven, knitted or non-woven fabrics above all are suitable here. Thus, for example, by appropriate treatment, it is possible to achieve the result that textiles of cellulose, synthetic fibers or fiber mixtures burn to a lesser degree than untreated textiles of the same type of fiber. The treatment of fiber materials by means of compositions which comprise phosphorus compounds is described, for example, in U.S. Pat. No. 2,926,145 and in U.S. Pat. No. 2,733,229.

U.S. Pat. No. 2,691,566 and U.S. Pat. No. 2,691,567 likewise describe compositions comprising phosphorus compounds, and their use for the treatment of textile materials. Flame-retardant properties are said to be imparted to the textiles by this process. According to U.S. Pat. No. 2,691,566, corresponding phosphorus compounds can be obtained by reaction of acid phosphoric acid diesters with dimers of diisocyanates, or by multi-stage reactions starting from substituted phosphoryl chlorides. In the latter synthesis, the corresponding chlorides are reacted with compounds containing hydroxyl groups. Reaction with the dimers of a diisocyanate is then carried out. The disadvantage of the products thus obtained is that deeply colored impurities which can be removed only with great difficulty, if at all, may be formed and contained in the reaction mixtures. Without their removal, however, the reaction products can be used for the treatment of fiber materials to only a very limited extent. They cannot be used for non-dyed textiles because of the dark color of the impurities. Another disadvantage of the preparation process described in U.S. Pat. No. 2,691,566 is that undesirable polymers, which are still contained in the end products, are formed in a manner which is uncontrollable or can be controlled only with difficulty.

With the compositions known to date which comprise phosphorus compounds, problems arise in respect of the effectiveness of the flame-resistant finish or in respect of the handle of the textiles treated with them or in respect of the permanence of the flame-retardant action after washing processes or in respect of the intrinsic color of these compositions. The inadequate permanence of flame-retardant finishes is a particular problem on fiber materials which consist of polyester fibers or which comprise polyester fibers as a mixture with other fibers. The not yet optimum action of (bromine-free) phosphoric acid esters known to date on polyester materials is mentioned in A. Püntener et al. *Melliand Textilbefichte* 5/1978, pages 412 to 415.

The present invention was therefore based on the object of providing compositions which cause a good flame-retardant action on fiber materials, lead to a pleasant handle of the finished goods, result in a satisfactory permanence of the flame-retardant action after washing processes and, if desired, can be prepared in a simple manner in a form which is free or virtually free from colored impurities or undesirable polymers.

The object was achieved by a composition obtainable by the following process steps a) reaction of a phosphite or of a mixture of phosphites of the general formula (I)

with an optionally substituted benzoquinone, naphthoquinone or anthraquinone or a mixture of such quinones b) reaction of the product obtained in process step a) with a mono-, di- or polyisocyanate or a mixture of such isocyanates, in which $R^1$ and $R^2$ independently of one another represent an alkyl radical having 1 to 8 C atoms or represent a phenyl radical, it being possible for this alkyl radical or phenyl radical to be substituted by one or more halogen atoms.

An advantageous and therefore preferred embodiment of the invention comprises a composition of the type mentioned, wherein unsubstituted p-benzoquinone or 1,2- or 1,4-naphthoquinone has been used in step a).

Preferred compositions according to the invention are those which are obtained by using not a monoisocyanate but a di- or polyisocyanate or a mixture of such polyfunctional isocyanates in process step b).

A further preferred embodiment comprises a composition of the type mentioned wherein $R^1$ and $R^2$ independently of one another represent an unsubstituted alkyl radical having 1 to 4 C atoms, or represent an unsubstituted phenyl radical, and another preferred embodiment comprises a composition of the type mentioned wherein both $R^1$ and $R^2$ represent a methyl radical. Dialkyl phosphites, in particular dimethyl phosphite, are accordingly preferably used for process step a).

A composition of the type mentioned, wherein, in process step b), a diisocyanate or a mixture of diisocyanates of the formula $$O=C=N-X-N=C=O$$

was used in which X represents

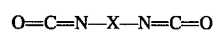

or represents

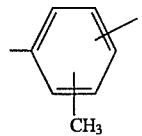

or represents

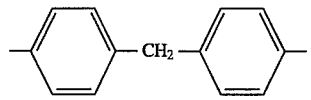

or represents

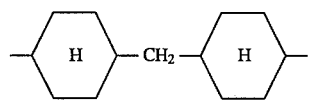

in which n is a number from 3 to 8, is another preferred embodiment of compositions according to the invention.

Compositions which can be obtained by using isophorone diisocyanate in process step b) are furthermore preferred.

By "isophorone diisocyanate" the following compound is meant:

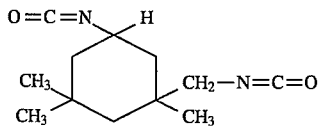

This compound is available from Hüls, DE. It has been found that the yellowing tendency of fiber materials treated with compositions according to the invention can be reduced if a molar excess of isophorone diisocyanate over the phosphoric acid triester obtained in step a) is used, in particular if 2,2 to 3,0 NCO groups of the isophorone diisocyante are employed per OH group of the phosphoric acid triester. Instead of monomeric isophorone diisocyanate its dimers, trimers or polymers may be used, in particular uretdiones which are formed from two molecules of isophorone diisocyanate by addition of a NCO group of the first molecule to a NCO group of the second molecule.

If desired, process step b) can be carried out in the presence of a compound $R^1OH$, in which $R^1$ has the meaning given in claim 1; that is, represents an alkyl radical having 1 to 8 C atoms, or represents a phenyl radical, it being possible for this alkyl radical or phenyl radical to be substituted by one or more halogen atoms.

A composition of the type mentioned in which the reaction in process step a) has been carried out at a molar ratio of phosphite:quinone of 1:0.5 to 1:1 is preferred. This molar ratio applies above all in the case where process step a) is carded out in water as the solvent. In contrast, if process step a) is carried out in an organic solvent or solvent mixture, in particular a solvent (mixture) of the type described in claim 4 and below in more detail, it is advisable to employ not 1 to 2 mol of phosphite (or phosphite mixture) per mol of quinone (or quinone mixture), as in the case of water as the solvent, but 1.1 to 1.25 mol of phosphite or phosphite mixture. The reaction can of course also be carried out in water in an advantageous manner with a molar ratio of 1.1:1 to 1.25:1.

Another preferred embodiment comprises a composition of the type mentioned, in which the reaction according to process step b) has been carried out such that 0.5 to 2.5 equivalents of isocyanate groups were used per equivalent of phosphite employed in step a).

It is particularly advantageous if the amount of isocyanate equivalents in process step b) is based on the equivalents of OH groups present in the main product formed in process step a). This may be illustrated by the example of the reaction of dimethyl phosphite and p-benzoquinone, in which the dimethyl p-hydroxyphenyl ester of phosphoric acid (called phosphoric acid hydroquinone ester or hydroquinone ester below) is formed as the main product. The starting compounds for the reaction of hydroquinone ester with isocyanate according to process step b) are preferably used in amounts such that 1.0 to 3.0, in particular 1.3 to 2.0 isocyanate groups are present per hydroxyl group of the phosphoric acid hydroquinone ester. The amount of polyvalent isocyanate required for this can be determined via quantitative NCO determination. If the hydroquinone ester is not employed in pure form, but in the form of the product mixture obtained according to process step a), the amount of hydroquinone ester in this mixture (yield of step a)) must be determined in order to determine the amount of this mixture which is preferably to be used for step b). The hydroquinone ester is determined quantitatively by gas chromatography (GC) or by high pressure liquid chromatography (HPLC).

Particularly preferred compositions of the type mentioned according to the invention are those in which, at the start of process step a), the pH of the reaction mixture was 7 to 8. In a number of cases, it is even essential to carry out process step a) such that the pH is 6.5 or higher, for example up to not more than 11, at the start of and during the reaction according to step a), because otherwise products with unsatisfactory properties are obtained. A composition of the type mentioned, in which a sulfite has been added to the reaction mixture towards the end of or after process step a), is likewise a preferred embodiment, especially if step a) was carried out in water as the solvent. In this case, the sulfite is preferably water-soluble. It is likewise preferable for the product obtained to have been recrystallized, in particular recrystallized from water, after process step a) and for only the recrystallized product to have been used for process step b). This embodiment is particularly expedient if process step a) has been carried out in water as the solvent.

The compositions according to the invention can be obtained by the process described in detail below:

The process for the preparation of the compositions according to the invention comprises process steps a) and b) as described in the patent claims.

In step a), a phosphite of the formula (I)

is reacted with a benzoquinone, naphthoquinone or anthraquinone. Instead of a single phosphite of the formula (I), a mixture of phosphites which all fall under formula (I) and differ, for example, in the nature of the radical $R^1$ and/or of the radical $R^2$ can also be used. The benzoquinone, naphthoquinone or anthraquinone employed for the reaction according to process step a) can be unsubstituted, but it can also contain one or more substituents on one or more aromatic rings. Possible substituents in this case are, in particular, chlorine or bromine atoms. If an anthraquinone is used, it is, for example, 9,10-anthraquinone. Preferably, however, an unsubstituted 1,4-benzoquinone (p-benzoquinone) or unsubstituted 1,2- or unsubstituted 1,4-naphthoquinone is employed as the quinone. Instead of a single quinone, it is also possible to use a mixture of quinones of the type mentioned.

The phosphites of the formula (I) are known compounds. The formula (I) takes account of the fact that the tautomeric equilibrium in phosphites lies predominantly on the side of this formula. The radicals $R^1$ and $R^2$ in formula (I) independently of one another represent a straight-chain or branched alkyl radical having 1 to 8 carbon atoms, or represent a phenyl radical. The corresponding alkyl radicals or phenyl radicals can contain one or more halogen atoms as substituents, in this case, in particular, chlorine or bromine atoms. Preferably, however, $R^1$ and $R^2$ independently of one another each represent an unsubstituted alkyl radical having 1 to 4 carbon atoms, or represent an unsubstituted phenyl radical. Particularly good results are obtained if both $R^1$ and $R^2$ represent $CH_3$.

A reaction of dialkyl phosphites with quinones such as is carried out in process step a) is known from the literature. Such reactions are described, for example, in "*J. Org. Ch.*" Volume 38, No. 12 (1973) pages 2151 et seq. "*J. Org. Ch.*", Volume 22 (1957) pages 1282/83, "*J. Amer. Chem. Soc.*", Volume 81 (1959), pages 4338 et seq., "Chemical Abstracts" 54, 20940 a and DE Patent Specification No. 937 956. In these documents, suitable conditions as to how step a) of the process leading to compositions according to the invention can be carried out are given, and products of such reactions are also described. As analyses have shown, mixtures of products are obtained in step a) of the process leading to compositions according to the invention. The nature and amount of the individual components of these mixtures depend on the process conditions chosen, in particular on the nature and ratios of the amounts of the starting substances. It is to be assumed that a phosphoric acid ester is formed as the main product by addition of the P-H compound (phosphite) onto the quinone system. If p-benzoquinone has been employed, an ester of the formula

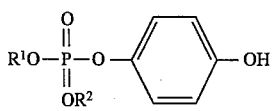

is accordingly formed as the main product. Other aromatic esters having free OH groups are formed correspondingly by reaction with other quinones.

For the reaction according to process step a), either amounts of quinone and phosphite which are equivalent to one another are expediently employed, or the reaction is carried out with an excess of phosphite. It is preferable to carry out process step a) with a molar ratio of phosphite to quinone of 1:0.5 to 1:1. This applies above all, as mentioned above, if water is used as the solvent. In the case of organic solvents, a molar ratio of phosphite (mixture) to quinone (mixture) of 1.1:1 to 1.25:1 is frequently expedient.

Process step a) can in principle be carried out in any desired solvent; methanol, for example, is particularly suitable. Even more favorable solvents (solvent mixtures) are described below. Water is also particularly suitable as a solvent at a temperature in the range from 40° to 80° C. In the case of dimethyl phosphite and p-benzoquinone as starting substances, this has the advantage that the main product formed during the reaction precipitates on cooling and can be purified conveniently and effectively by recrystallization, in particular from water. In this procedure, it is expedient to employ only the colorless or virtually colorless product which has been purified by recrystallization for the subsequent process step b) (reaction with di- or polyisocyanates) and to discard or use elsewhere the filtrate obtained after recrystallization.

Instead of water or methanol as the solvent for process step a), other solvents or mixtures thereof, which are mentioned in claim 4, have proved to be particularly suitable. Particularly preferred embodiments of compositions according to the invention are accordingly obtained by a procedure in which process step a) is carried out in a compound $R^3OR^5$, a compound $R^5OR^5$, a compound $R^5COOR^5$ or in a compound $(R^3O)_x(R^4O)_{3-x}P=O$ or a mixture of such compounds as the solvent, in which each radical $R^3$ present is an optionally substituted phenyl or naphthyl radical and each radical $R^4$ present is an unbranched or branched alkyl radical having 1 to 18, preferably 4 to 12 carbon atoms, each radical $R^5$ present is an alkyl radical having 1 to 6 carbon atoms, and in which x represents 0, 1, 2 or 3. If one of the compounds mentioned contains several radicals $R^3$ or several radicals $R^4$ or several radicals $R^5$ in one molecule, these radicals $R^3$ or $R^4$ or $R^5$, in each case belonging to the same group, can in each case be identical to or different from one another.

Particularly suitable solvents for carrying out process step a) are phosphoric acid triesters of the general formula $(R^3O)_x(R^4O)_{3-x}P=O$, which are described below in more detail. In addition to these phosphoric acid triesters, particularly suitable solvents are ethers of the general formulae $R^3OR^5$ or $R^5OR^5$ or esters of the formula $R^5COOR^5$. These ethers $R^3OR^5$ or $R^5OR^5$ or esters of the formula $R^5COOR^5$ can even bring even more advantageous results than the phosphoric acid triesters $(R^3O)_x(R^4O)_{3-x}PO$ in certain cases, and in particular in respect of the handle of sheet-like structures of fiber materials which have been treated with compositions according to the invention. Above all, if phosphoric acid triesters are employed as the solvent and are not removed completely after the preparation of compositions according to the invention, the handle of treated textiles of polyester fibers is not as pleasant under certain circumstances as in the case where compounds of the formulae $R^3OR^5$, $R^5OR^5$ and $R^5COOR^5$ are used.

In the formulae mentioned, all the radicals $R^3$ independently of one another in each case represent a phenyl or naphthyl radical, which can carry substituents, and all the radicals $R^4$ independently of one another in each case represent an unbranched or branched alkyl radical having 1 to 18 carbon atoms. Preferably, all the radicals $R^4$ present contain 4 to 12 carbon atoms. The value of x in the phosphoric acid triesters which are suitable as solvents can be 0, 1, 2 or 3.

Particularly suitable representatives of the compounds $(R^3O)_x(R^4O)_{3-x}P=O$, that is to say of the phosphoric acid triesters which are particularly suitable as solvents for process step a), are triaryl phosphates, such as, for example, triphenyl phosphate ($R^3=C_6H_5$, x=3) or diaryl alkyl phosphates, for example n-butyl diphenyl phosphate ($R^3=C_6H_5$, $R^4$=n–$C_4H_9$, x=2) or trialkyl phosphates, such as tri-n-butyl phosphate ($R^4$=n–$C_4H_9$, x=0). In each case, $R^3$ is a phenyl radical or a naphthyl radical; however, the radical $R^3$ can contain substituents, such as, for example, alkyl groups having 1 to 4 C atoms. $R^3$ can represent an optionally substituted 1-naphthyl or 2-naphthyl radical. The radical $R^4$ is an alkyl radical having 1 to 18 C atoms, which can be branched or unbranched. In the case where several $R^3O$ groups (x=2 or 3) or several $R^4O$ groups (x=0 or 1) are present in the compounds $(R^3O)_x(R^4O)_{3-x}P=O$ which are suitable as solvents, the individual radicals $R^3$ or $R^4$ can of course differ from one another. Preferred phosphoric acid triesters are those in which all the radicals $R^3$ in each case represent an unsubstituted phenyl radical and all the radicals $R^4$ in each case represent a branched or unbranched alkyl radical having 4 to 12 C atoms. Instead of a single phosphoric acid triester of the formula $(R^3O)_x(R^4O)_{3-x}PO$, it is of course also possible to employ a mixture of compounds which all fall under this formula.

The compounds $R^3OR^5$, $R^5OR^5$ and $R^5COOR^5$ which are suitable as solvents in addition to the phosphoric acid triesters $(R^3O)_x(R^4O)_{3-x}P=O$ are ethers or esters which are liquid at room temperature under normal pressure in the normal case. $R^3$ in these formulae has the same meaning as stated above for the phosphoric acid triesters. All the radicals $R^5$ present in each case represent an unbranched or branched alkyl radical having 1 to 6 carbon atoms. Particularly suitable representatives of the ethers or esters mentioned are n-butyl acetate, diethyl ether and anisole.

In some cases it may be advantageous to use solvents in which the phosphoric acid esters obtained by step a) are insoluble or essentially insoluble.

It has been found that an advantageous embodiment of the compositions according to the invention comprises carrying out process step a), that is to say the reaction of phosphite(s) with quinone(s), in certain phosphoric acid esters described above in more detail or in the other ethers or esters mentioned, as the solvent. It has been found that the yield of reaction product in this case, that is to say a phosphoric acid triester of the formula $(R^1O—)(R^2O—)(HOC_6H_4—O—)P=O$, can be increased up to 90% or more, and that it is not necessary to isolate this phosphoric acid triester before the reaction with isocyanate (process step b). The statement made above that an ester of the formula $(R^1O)(R^2O)(HOC_6H_4O)P=O$ is formed as the main product in process step a) applies in the case where a phosphite has been reacted with p-benzoquinone in step a). The radical $HOC_6H_4O$ is in this case a radical derived from hydroquinone by removal of a hydroxyl hydrogen atom. In the case where another quinone has been employed in process step a), and not p-benzoquinone, corresponding phosphoric acid esters of other aromatic dihydroxy compounds of course result, these being formed by addition of the P-H unit of the phosphite of formula I onto the unsaturated C=O bond system of the quinone in question. For simplicity, however, only the hydroquinone ester formed from p-benzoquinone will be mentioned below as representative of these compounds. The ester formed in step a) does not have to be isolated, as mentioned, if step a) has been carried out in an organic solvent or solvent mixture of the type mentioned; rather, process b) can be carried out directly with the product mixture obtained according to process step a), if appropriate after a purification operation, which comprises, for example, adding active charcoal and filtering.

The concentration of the phosphite or phosphite mixture of the formula I and of the quinone or quinone mixture in the solvent (phosphoric acid triester or other esters or ethers) is not particularly critical for carrying out process step a). It should be chosen such that a reaction procedure in a homogeneous phase is possible. In the case where compounds $R^3OR^5$, $R^5OR^5$ or $R^5COOR^5$ are used as solvents, it has been found that it is often favorable, in order to achieve high yields, to carry out process step a), using a molar ratio of quinone to solvent of 1:5 to 1:50.

It is indeed advantageous but not absolutely necessary for the solvent (mixture) $R^3OR^5$, $R^5OR^5$, $R^5COOR^5$ or $(R^3O)_x(R^4O)_{3-x}P=O$ to be liquid at room temperature, since, if a solvent which is solid at room temperature is used, the reaction according to process step a) can also be carried out at a higher temperature, at which the solvent (mixture) is present in liquid form.

From the point of view of the economy of the process, in the case where organic solvents are employed for process step a), it is favorable for the product (mixture) formed according to process step a), that is to say one or more phosphoric acid hydroquinone esters of the formula $((R^1O)(R^2O)(HOC_6H_4O)P=O$, not to be isolated but for the solution, obtained according to step a), of this ester or ester mixture in $R^3OR^5$, $R^5OR^5$, $R^5COOR^5$ or $(R^3O)_x(R^4O)_{3-x}PO$ as the solvent to be used directly for the reaction with isocyanate in accordance with process step b). Nevertheless, in certain cases it is advisable to add an adsorbent before carrying out process step b), subsequently to filter the mixture and to use the filtrate for process step b). This is expedient and under certain circumstances even necessary if the compositions according to the invention are to be employed later for the treatment of undyed textiles. More or less intensely colored by-products can be formed in process step a), depending on the starting substances and reaction conditions. These by-products can be removed from the solutions by addition of known adsorbents, if appropriate at elevated temperature, and subsequent filtration. Pulverulent or granular active charcoal is particularly suitable as the adsorbent.

As mentioned above, a favorable temperature range for the reaction according to process step a) is 40° to 80° C. if the step is carried out in water as the solvent. If organic solvents of the type mentioned are used, the reaction can already proceed, if appropriate, at room temperature at an acceptable rate, especially if a catalyst of the type described below is used. If desired, if organic solvents are used, process step a) can also be carried out at elevated temperature, for example at 30° to 50° C.

Process step a) is preferably carried out in an approximately neutral to basic medium. At the start of the reaction in particular, the pH should be 7.0 to 8.0. It should not fall below 6.5 during the reaction, and a pH of 7.0 to 11.0 is preferably maintained while carrying out process step a). The adjustment and maintenance of a desired pH can be effected by addition of bases. Alkali metal hydroxides or alcoholates, such as sodium hydroxide or sodium methylate, are suitable in certain cases. However, these inorganic bases are less preferred. Organic nitrogen bases are particularly favorable bases, which simultaneously act as catalysts for the reaction of phosphite with quinone. Amines and alkanolamines, in particular tertiary amines of the formula $(R^6)_3N$, in which all the radicals $R^6$ independently of one another in each case represent an alkyl radical having 1 to 4 carbon atoms or represent $—CH_2CH_2OH$, are particularly suitable for this purpose. In addition, tertiary amines having cycloaliphatic radicals bonded to N, such as dimethylcyclohexylamine, are particularly suitable. Triethylenediamine, a ditertiary diamine in which two N atoms are joined to one another via three ethylene bridges, is also particularly suitable. If process step a) is carried out in water, tertiary alkanolamines, such as triethanolamine, are particularly suitable. If the step is carried out in organic solvents, tris-alkylamines, such as triethylamine, or the other tertiary amines mentioned are particularly favorable. Furthermore, substituted ethylene diamines in which substituents are bonded to one or both nitrogen atoms are suitable. Suitable substituents are alkyl radicals having 1 to 4 C-atoms which may carry substituents, for example hydroxyl groups. Such products are commercially available, for example Quadrol L (BASF AG) or Pluriol P (BASF AG).

As analyses have shown, mixtures of products can be obtained in step a) of the process leading to compositions according to the invention. The nature and amount of the individual components of these mixtures depend on the process conditions chosen, in particular on the nature and ratios of the amounts of the starting substances. It is to be assumed that addition of the P-H compound (phosphite) onto the quinone system takes place. In the case of addition of a phosphite $(R^1O)(R^2O)P(O)H$ onto p-benzoquinone, it can be detected by analysis that the product

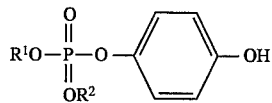

is formed in a considerable proportion. Esters having free OH groups are formed in a corresponding manner in the reaction with other quinones.

If process step a) has been carried out in water as the solvent, recrystallization may be appropriate, as mentioned, before carrying out step b). If an organic solvent has been used, it is often favorable, as also mentioned, not to isolate the product from step a) (hydroquinone ester of phosphoric acid), but is appropriate to remove impurities by means of addition of active charcoal. In both cases, a sulfite can be added for the purpose of purification. Moreover, it is often favorable to add to the reaction mixture relatively small amounts of methanol or ethanol, for example 0.5 to 10% by weight, based on the total mixture, after process step a) has ended and before, during or after carrying out process step b). The mixtures can in this case be maintained better in a liquid, homogeneous form, and eventually in a more stable form. In addition to methanol or ethanol, tri-n-butyl phosphate can be added for the same purpose.

It is advantageous to carry out process step a) in an approximately neutral to alkaline medium, that is to say in a pH range of 6.5 or higher, and at the start of the reaction in particular, the pH should be in the range from 7 to 8. If appropriate, it can be adjusted by corresponding additions, for example of triethanolamine or other abovementioned amines. It is furthermore advisable not to allow the pH to fall below 6.5 during the reaction according to process step a), and preferably to maintain a pH of 7 to 11 during the reaction, for example by addition of base at certain time intervals. If the reaction according to process step a) is carried out in an organic solvent and not in water, the pH is determined on a 1:1 mixture (based on the volume) of a sample of the reaction solution and water.

Instead of the recrystallization already mentioned in the case where water is the solvent, the main product formed in process step a) can also be obtained in a colorless or almost colorless form by another measure, if this is desired. This measure comprises adding a reducing agent to the reaction mixture towards the end of process step a), that is to say when 90% or more of the starting substance has already reacted. This addition of reducing agent can also be carded out after process step a) has ended. The amount of reducing agent is expediently chosen according to the desired effect, and in the normal case 5 to 10% of the amount equivalent to the quinone originally employed is sufficient to obtain an almost colorless or colorless reaction product. After addition of the reducing agent, the reaction mixture can be left at elevated temperature for a certain further period of time, in order to accelerate the formation of a colorless product. Sulfites, for example water-soluble sulfites such as sodium sulfite, in particular, are especially suitable as reducing agents.

The second step of the process by which compositions according to the invention can be obtained comprises reacting the product obtained after carrying out process step a) (a phosphoric acid triester in which at least one of the three alcohol components of the triester contains an aromatic OH group originating from the reaction with quinone, for example a phosphoric acid hydroquinone ester) with a monoisocyanate, diisocyanate or polyisocyanate or a mixture of such isocyanates, As mentioned above, it is not essential to use the entire product mixture obtained according to step a) for process step b). Rather, it may be desirable and expedient to use only the purified main product, for example the product or product mixture obtained by recrystallization, for step b).

Preferred compositions according to the invention are obtained by a procedure in which exclusively polyfunctional isocyanates, that is to say di- or polyisocyanates, in particular di- or trifunctional isocyanates, or mixtures of polyfunctional isocyanates are employed in process step b). Less preferred compositions according to the invention can be obtained by employing monoisocyanates in process step b), or mixtures of isocyanates containing monoisocyanates. Monoisocyanates in connection with the invention are understood as meaning compounds of the formula RNCO, in which R represents an aliphatic or cycloaliphatic radical or represents a phenyl radical. In the case of aliphatic radicals, R has 1 to 18 carbon atoms, and cycloaliphatic radicals R have up to 8 carbon atoms in the ring, in particular 5 or 6 carbon atoms, in the normal case. The radicals R can carry substituents, for example halogen atoms. If monoisocyanates of the formula RNCO are to be used for the preparation of compositions according to the invention, n-propyl isocyanate, n-butyl isocyanate or stearyl isocyanate are preferred.

The reaction according to process step b), like that according to step a), usually leads to a product mixture, the composition of which depends on the nature and ratio of the amounts of the compounds employed and on the reaction conditions. This is confirmed by analysis, for example by HPLC (high pressure liquid chromatography).

The di- or polyisocyanates which are preferably to be employed in step b) are organic compounds in which at least two N=C=O groups are bonded to divalent or polyvalent radicals. A diisocyanate of the formula shown below or a mixture of several diisocyanates which fall under this formula is preferably used:

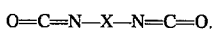

O=C=N—X—N=C=O.

The radical X in this formula can be, for example, an unsubstituted divalent alkylene or cycloalkylene radical, and in this case it preferably contains 2 to 8 carbon atoms; compounds which are particularly suitable are, for example, those in which X represents —(CH$_2$)$_n$—, in which n represents a number from 3 to 8. The radical X can be saturated or unsaturated and contain one or more substituents. Polyfunctional isocyanates in which X is a divalent, optionally substituted aromatic radical, that is to say an aryl or aralkyl radical, in particular a radical of the formula

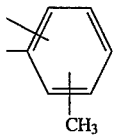

that is to say a toluylene radical, or of the formula

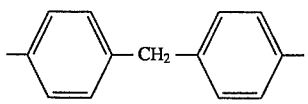

are particularly preferred.

The diisocyanate in which X represents

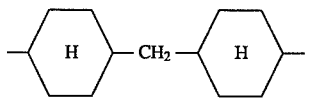

is also particularly suitable.

In addition, isophorone diisocyanate has proved to be particularly suitable.

Other polyfunctional isocyanates, which are described below in more detail, are furthermore particularly suitable for carrying out process step b). The use of these isocyanates has proved to be particularly appropriate for the reaction with products (hydroquinone esters) which are obtained after carrying out step a) in (R$^3$O)$_x$(R$^4$O)$_{3-x}$P=O as the solvent. These particularly suitable polyfunctional isocyanates are products which are formed by reaction of 1,1,1-trimethylolpropane CH$_3$CH$_2$C(CH$_2$OH)$_3$ with a toluene diisocyanate, it also being possible for the toluene diisocyanate used to be a mixture of various isomers. In particular, toluene 2,4-diisocyanate, toluene 2,6-diisocyanate or a mixture of these isomers, for example in a ratio of 80 parts of the 2,4-isomer to 20 parts of the 2,6-isomer, can have been reacted with trimethylolpropane for this purpose. Preferably, about 3 mol of toluene diisocyanate per mol of trimethylolpropane are employed for this reaction (although other ratios of amounts are also possible), so that, in accordance with the following reaction equation

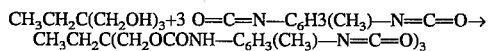

a product which has three free isocyanate groups and can react with the hydroquinone ester, described above, from process step a) is formed. In reality, the situation is more complicated, since side and secondary reactions, for example reactions of the NCO groups with one another, proceed when trimethylolpropane is reacted with a toluene diisocyanate or a mixture of isomeric toluene diisocyanates. It is therefore possible that the reaction products of 1 mol of trimethylolpropane and 3 mol of toluene diisocyanate contain less than the number of 3 NCO groups per molecule to be expected in theory. Suitable reaction products of trimethylolpropane and toluene diisocyanate are commercially available products, for example Desmodur L 75 from Bayer AG or Polurene AD from S.A.P.I.C.I. Spa (Italy).

A procedure which is described below in more detail is even more favorable than the use of the abovementioned reaction products of trimethylolpropane and toluene diisocyanate for carrying out process step b). This procedure comprises first reacting the product from process step a) (hydroquinone ester) with a polyfunctional isocyanate, for example toluene diisocyanate, in process step b) in ratios of the amounts such that free isocyanate groups are still present in the reaction product, which are then reacted with a polyhydric alcohol, in particular trimethylolpropane. It is favorable here to carry out process step b) such that 1.3 to 3.0 equivalents of isocyanate groups, that is to say 1.3 to 3.0 equivalents of NCO, are present per equivalent of OH groups of the reaction product from process step a). These OH groups are hydroxyl groups bonded to aromatic rings, which are formed by addition of the structural unit —P—H onto quinone. It is particularly favorable if 1.3 to 2.0 NCO groups of the di- or polyisocyanate, for example of a toluene 2,4— or 2,6-diisocyanate of the type mentioned above or of a mixture thereof, are present per OH group of the reaction product of step a). After process step b), the addition product obtained in this step, which still contains free isocyanate groups originating from the polyfunctional isocyanate, is reacted with a polyhydric alcohol, in particular 1,1,1-trimethylolpropane, expediently in ratios of amounts such that no further free NCO groups are present after this reaction.

The reaction according to process step b) can be carried out such that only the product (mixture) obtained according to process step a) and polyfunctional isocyanate are reacted with one another, if appropriate in the presence of a solvent and/or a catalyst, as described below in more detail. However, a compound $R^1$—OH can additionally also be employed in step b), this being added to the reaction mixture before or during the reaction. Further variants of compositions according to the invention can be obtained in this manner. The amount of compound $R^1$—OH additionally added should expediently be chosen such that not more than 50% of all the isocyanate groups present can react with $R^1$—OH, that is to say the equivalents of $R^1$—OH should be not more than 50% of the equivalents of N=C=O groups. In the compound $R^1$—OH, $R^1$ has the same meaning as has been stated above and in claim 1 for the phosphites which are used as starting substances.

The reaction according to process step b) can be carried out in a solvent, for example in ethyl acetate, or in a ketone, such as methyl ethyl ketone. However, it is also possible to carry out the reaction without solvents; in this case, the reaction is carded out, for example, at a temperature above the melting point of the starting substances employed for step b). The procedure without solvents has the advantage that the end product obtained, that is to say the composition according to the invention, can then be dissolved or dispersed directly in that solvent from which the treatment of the fiber materials with the compositions is to be carried out, without a different solvent having to be removed beforehand.

If the reaction is to be carried out with solvents, n-butyl acetate or phosphoric acid triesters $(R^3O)_x(R^4)_{3-x}P=O$, as are described above, can also be employed, in addition to ethyl acetate or ketones.

If process step a) has been carried out in water as the solvent, the water is removed before process step b), in order to prevent the isocyanate from reacting with the water.

For the reaction of the hydroquinone ester with the isocyanate in accordance with process step b), the starting compounds are preferably used in amounts such that 1.0 to 3.0, in particular 1.3 to 2.0 isocyanate groups are present per hydroxyl group of the phosphoric acid hydroquinone ester. If it is necessary to determine the amount of polyfunctional isocyanate required for this purpose, for example in the case of the reaction product obtained from trimethylolpropane and toluene diisocyanate, this can be carried out via quantitative NCO determination. If the hydroquinone ester is not employed in the pure form but in the form of the product mixture obtained according to process step a), without prior isolation, the amount of hydroquinone ester in this mixture (yield from step a)) must be determined in order to determine the amount of this mixture which is preferably to be used for step b). Quantitative determination of the hydroquinone ester is carried out by gas chromatography (GC) or by high pressure liquid chromatography (HPLC).

Process step b) is preferably carried out in the presence of a catalyst, and suitable catalysts for this purpose are trialkylamines or dialkyltin(IV) salts. $Sn^{II}$ salts, such as tin octoate, are also suitable.

It may be expedient to carry out process step b) under conditions such that isocyanate groups which are still present in the mixture at the end of the reaction, for example if an excess of isocyanate equivalents is used, are not present in the free form. Rather, these isocyanate groups can be blocked, either in a known form by addition of oximes or by dimerization or trimerization. This blocking as a result of dimerization or trimerization of isocyanate groups with one another can be achieved, for example, by addition of catalysts. Suitable measures are described in U.S. Pat. No. 2,691,566 and in J. H. Saunders et al. "Polyurethanes, Chemistry and Technology, Part I. Chemistry", Robert E. Krieger Publishing Company, Malabar, Florida, Reprint Edition 1987, pages 90 et seq. In the case where no free NCO groups are desired, oximes or the dimerization or trimerization catalysts mentioned are thus added towards the end of or after carrying out process step b).

Another possibility of removing free isocyanate groups which are still present comprises reacting them with compounds containing hydroxyl groups, such as butanol or trimethylolpropane.

As well as removing free isocyanate groups, it may be desirable for residues of unreacted product from process step a) (hydroquinone ester) also to be removed after carrying out process step b). This can be effected by means of addition of a monoisocyanate RNCO of the type described above, and in certain cases can lead to an improvement in the properties of sheet-like structures of fiber materials which have been treated with compositions according to the invention.

If appropriate, the reaction of process step b) can already proceed at room temperature at an acceptable rate, especially if catalysts such as trialkylamines or tin salts are present. If desired, however, it can also be carried out at elevated temperature, for example in the range from 30° to 100° C.

After carrying out process step b), the resulting compositions according to the invention can be put to further use, for example for the treatment of fiber materials such as textiles, in order to impart to these flame-retardant properties. It is to be assumed that one of the main components of the compositions according to the invention is the product of the reaction of a compound having a free hydroxyl group with an isocyanate, preferably a polyfunctional isocyanate, this compound having the free hydroxyl group resulting from the reaction according to process step a). The main component of compositions according to the invention would accordingly contain at least one phosphoric acid triester unit, one aromatic group originating from the quinone and one urethane unit.

The compositions according to the invention are outstandingly suitable for the treatment of fiber materials, in particular of sheet-like structures of fiber materials. The sheet-like structures can be, for example, woven fabrics, knitted fabrics or non-woven materials such as fiber fleeces. Sheet-like structures which comprise polyester fibers in a considerable proportion, for example up to 70 to 100% by weight, are particularly preferred for the treatment with compositions according to the invention. The remaining 0 to 30% by weight comprises, for example, cotton. Possible polyester fibers for this purpose are, above all, fibers of polyethylene terephthalate. The term fibers used here of course includes both staple and spun fibers, and also continuous filaments.

The compositions according to the invention are employed in the form of solutions or dispersions for the treatment of fiber materials, for example of textile sheet-like structures. Possible solutions are, above all, solutions in methanol, and possible dispersions are, above all, dispersions in water. In addition to compositions according to the invention and, if appropriate, other additions customary for the treatment of fiber materials, these also comprise, in the normal case, one or more dispersing agents; for example, surface-active nonionic products, such as ethoxylated fatty alcohols or ethoxylated fatty acids, are suitable. In this case, also highly ethoxilated products, for example products with an average of up to 60 $CH_2CH_2O$— units per molecule, can be suitable. It has proved to be particularly advantageous additionally to add one or more phosphoric acid triesters, the alcohol components of which are chosen from phenol, resorcinol or hydroquinone, to the aqueous dispersions. However, the compositions according to the invention can also be employed in an advantageous manner for the treatment of the fiber materials in the form of a solution in an organic solvent. Possible solvents are, for example, alcohols, esters or ketones, in particular solvents which can readily be removed again because of their low boiling point, such as, for example, methanol. Dimethylsulfoxide can also be used. Good flame-retardant properties with a good permanence toward washing processes are imparted to the fiber materials treated with compositions according to the invention and after-treated in a known manner, especially in the case of materials comprising polyester.

In the case where the phosphoric acid ester, for example hydroquinone ester, formed in process step a) is not isolated, compositions according to the invention can be obtained, where appropriate, as solutions in $(R^3O)_x(R^4O)_{3-x}PO$, $R^3OR^5$, $R^5OR^5$ or $R^5COOR^5$. If they are to be employed in the form of aqueous dispersions for the treatment of fiber materials, these dispersions can be obtained by addition of water and a dispersing agent and possibly, if desired, removal of the organic solvent. If they are to be applied to the fiber materials in the form of a solution in an organic solvent, for example methanol, this solvent is added after the end of the process step b), the organic solvent, for example $R^3OR^5$, likewise having been removed beforehand, if appropriate.

The compositions according to the invention are applied in the form of a dispersion or solution in water or an organic solvent, for example methanol, to a fiber material in order to impart to this flame-retardant properties. The application can be carried out by known methods, preferably by padding. In this process, the liquors expediently comprise about 100 to 300 g/l of the composition according to the invention or of a mixture of compositions according to the invention. In addition, they can also comprise other products usually used for the treatment of fiber materials or textiles, for example antistatics or agents which impart a soft handle. During padding, for example, the fiber material can be squeezed off to the extent that, before drying, it has absorbed 40 to 80% by weight, or more, depending on the material, of its own weight of treatment liquor. The material is dried under the customary conditions, for example at 80° C./10 minutes to 150° C./10 minutes. Fabrics finished in this way show a good permanence of the flame-retardant action even after several washes at 60° C. The permanence even may exist after one to several washes at the boil, depending on the products employed. If compositions according to the invention are employed in the form of aqueous dispersions, the treatment of the fiber materials can also be carried out by an exhaustion process under certain circumstances. This is possible in a number of cases if, for example, certain ethoxylated alcohols are used.

Further advantageous possible uses of compositions according to the invention comprise application of compositions according to the invention to fiber materials in combination with other products, simultaneously or in succession. These other products, for example, can themselves also impart flame-retardant actions. The combination of compositions according to the invention with N-methyloldialkylphosphonopropionamides has proved to be very suitable. This combination can be readily employed for the treatment of blended fabrics. A possibility in this context comprises, for example, the following two procedures:

a) Blended fabrics of polyester/cotton are treated with solutions of compositions according to the invention (padder), the blended fabric having been treated beforehand with the known flame-retardant agent N-methylol-dimethylphosphonopropionamide, as described, for example, in AT Patent Specification No. 269 058 (Ciba AG), b) a blended fabric of 80% cotton and 20% polyamide which has been pretreated with N-methylol-dimethylphosphonopropionamide is treated with a solution of a composition according to the invention.

The invention will now be illustrated by embodiment examples.

EXAMPLE 1

Dimethyl phosphite and p-benzoquinone were first reacted with one another by the following process, it being assumed that a hydroquinone ester of the formula

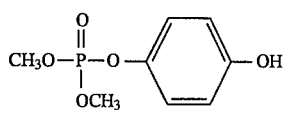

was formed as the main product. In the following statements, it is therefore assumed that this ester was formed as the main product.

1 mol of p-benzoquinone was added to 1.5 mol of dimethyl phosphite in 3600 g of water at room temperature. After addition of 0.13 mol of triethanolamine, the reaction started. In the course of the reaction, the pH dropped and the rate of reaction decreased. The rate of reaction could be increased again by addition of a further 0.13 mol of triethanolamine. When the reaction had ended, the mixture was heated up to about 75° C., and 0.08 mol of sodium sulfite in solid form was added. After about 5 minutes, the mixture was cooled to about 20° C. Before the reaction (process step b) (2nd stage) of the ester of the above formula with diisocyanate, the ester, which precipitates out of the aqueous solution, was isolated and dried.

A mixture of 218 g (1 mol) of the ester of the above formula, 174 g (1 mol) of m-toluylene diisocyanate and 1510 g of ethyl acetate was heated to 70° C. After addition of a little amount of triethylamine (catalyst), the mixture was stirred at 70° C. for a further hour. 1235 g of methanol were then added. The resulting solution was applied to a fabric of 100% polyester by means of padding (liquor pick-up 90%) at room temperature. The fabric was dried at 110° C. for 10 minutes. The composition applied by padding had the effect of a good flame-retardant action in comparison with a non-padded sample of fabric of the same material. This flame-retardant action was retained in full even after several 60° C. washes.

EXAMPLE 2 (Reaction with diisocyanate without an additional solvent)

218 g (1 mol) of the ester of Example 1 obtained from dimethyl phosphite and p-benzoquinone were heated to about 80° C. 174 g (1 mol) of m-toluylene diisocyanate were then added. After dropwise addition of catalytic amounts of triethylamine, the mixture was stirred at 80° C. for a further hour. 2774 g of methanol were then added. The subsequent procedure and the results obtained by this procedure corresponded to the statements in Example 1.

EXAMPLE 3

218 g (1 mol) of the ester of Example 1 obtained from dimethyl phosphite and p-benzoquinone were initially introduced into the reaction vessel and heated to 80° C. 250 g (1 mol) of diphenylmethane 4,4'-diisocyanate were then added. After dropwise addition of catalytic amounts of dibutyltin dilaurate, stirring was continued at 80° C. for a further 4 hours, and 1404 g of dimethyl sulfoxide were then added. The resulting solution was applied to a blended fabric of 70% cotton and 30% polyester by means of padding (liquor pick-up about 90% by weight). The blended fabric had been pretreated beforehand with N-methylol-dimethyl-phosphonopropionamide. After padding, the fabric was dried at 110° C. for 10 minutes. The flame-retardant properties imparted by the treatment were retained in full even after several washes at the boil.

EXAMPLE 4

A mixture of 4.32 g of p-benzoquinone and 185.9 g of n-butyl acetate were heated to 40° C. 5.50 g of dimethyl phosphite were then added. After addition of 0.30 g of triethylenediamine N$_2$(CH$_2$CH$_2$)$_3$, an exothermic reaction started. After the evolution of heat had subsided, the mixture was stirred for a further 2 hours, a little active charcoal was added, and the mixture was heated to 70° C., kept at about 70° C. for 5 minutes and then filtered.

6.96 g of an 80:20 mixture of toluene 2,4- and 2,6-diisocyanate were added to the filtrate. The mixture was heated to about 70° C., and a few drops of dibutyltin dilaurate were added. After about 20 minutes 1.79 g of 1,1,1-trimethylolpropane were added. 4.45 g of n-butanol were added to the reaction mixture obtained, after which a clear solution resulted.

About 163 g of butyl acetate were distilled off from the resulting mixture. After addition of 23.2 g of methanol, the resulting solution was applied to an undyed woven fabric and to blue-dyed knitted goods, in each case of 100% polyester. The wet pick-up (after squeezing off and before drying), was about 100%, based on the woven fabric weight or the weight of the knitted goods. Drying was carried out at 110° C. for 10 minutes. The combustibility test showed a very good flame-retardant action both without prior washing of the polyester goods and after 20 mild washes (30° C., domestic washing machine, detergent).

We claim:

1. A composition made by the process comprising
    a) reacting a phosphite or a mixture of phosphites of the formula (I)

in which R$^1$ and R$^2$ independently of one another represent an alkyl radical having 1 to 8 C atoms or a phenyl radical, which alkyl or phenyl radicals are unsubstituted or substituted by one or more halogen atoms,
    with a benzoquinone which is unsubstituted or substituted by one or more chlorine or bromine atoms, a naphthoquinone which is unsubstituted or substituted by one or more chlorine or bromine atoms, or an anthraquinone which is unsubstituted or substituted by one or more chlorine or bromine atoms, or a mixture of such quinones, then
    b) reacting the product obtained in process step a) with a diisocyanate selected from the group consisting of isophorone diisocyanate and diisocyanates of the formula

O=C=N—X—N=C=O in which X is

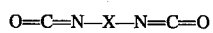,

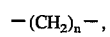

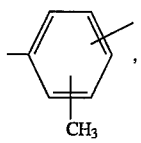,

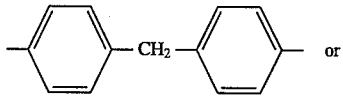 or

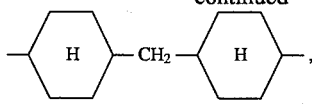

wherein n is a number from 3 to 8,
or a polyisocyanate or a mixture of such isocyanates.

2. A composition as claimed in claim 1 wherein unsubstituted p-benzoquinone or 1,2- or 1,4-naphthoquinone is used in step a).

3. A composition as claimed in claim 1, wherein the pH of the reaction mixture at the start of process step a) is 7 to 8.

4. A composition as claimed in claim 1, wherein process step a) is carried out in a compound $R^3OR^5$, a compound $R^5OR^5$, a compound $R^5COOR^5$ or in a compound $(R^3O)_x(R^4O)_{3-x}P=O$ or a mixture of such compounds as the solvent, in which each radical $R^3$ present is a phenyl or naphthyl radical and each radical $R^4$ present is an unbranched or branched alkyl radical having 1 to 18, carbon atoms, each radical $R^5$ present is an alkyl radical having 1 to 6 carbon atoms, and in which x represents 0, 1, 2 or 3.

5. A composition as claimed in claim 1, wherein the di-or polyisocyanate is reacted in process step b) with a product obtained in process step a) in a ratio of amounts such that 1.3 to 3.0 equivalents of isocyanate groups are present per equivalent of hydroxyl groups of the reaction product from process step a), and after process step b), the excess isocyanate groups originating from the di- or polyisocyanate are reacted with a polyhydric alcohol.

6. A composition as claimed in claim 4, wherein each radical $R^4$ present is an unbranched or branched alkyl radical having 4 to 12 carbon atoms.

7. A composition as claimed in claim 5, wherein a toluene diisocyanate is reacted in process step b) with a product obtained in process step a) in a ratio of amounts such that 1.3 to 3.0 equivalents of isocyanate groups are present per equivalent of hydroxyl groups of the reaction product from process step a), and after process step b), the excess isocyanate groups originating from the toluene diisocyanate are reacted with a polyhydric alcohol.

8. A composition as claimed in claim 5, wherein the di- or polyisocyanate is reacted in process step b) with a product obtained in process step a) in a ratio of amounts such that 1.3 to 2.0 equivalents of isocyanate groups are present per equivalent of hydroxyl groups of the reaction product from process step a), and after process step b), the excess isocyanate groups originating from the di- or polyisocyanate are reacted with a polyhydric alcohol.

9. A composition as claimed in claim 5, wherein the di- or polyisocyanate is reacted in process step b) with a product obtained in process step a) in a ratio of amounts such that 1.3 to 3.0 equivalents of isocyanate groups are present per equivalent of hydroxyl groups of the reaction product from process step a), and after process step b), the excess isocyanate groups originating from the di- or polyisocyanate are reacted with 1,1,1-trimethylolpropane.

* * * * *